US00PP10420P

United States Patent [19]

Lemon

[11] Patent Number: Plant 10,420

[45] Date of Patent: May 26, 1998

[54] VARIETY OF GERANIUM PLANT NAMED 'MAIDEN LILAC'

[75] Inventor: David Lemon, Lompoc, Calif.

[73] Assignee: John Bodger & Sons Company, So. El Monte, Calif.

[21] Appl. No.: 724,704

[22] Filed: Oct. 1, 1996

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Fulwider Patton Lee Utecht, LLP

[57] ABSTRACT

The cultivar is characterized by its compact medium green foliage and vivid lavender bloom. Its strong growth habit, quick rooting time and continuous flowering provide for superb cuttings and also for quick recovery following wet weather conditions. The blooms exhibit good post-harvest quality.

1 Drawing Sheet

BACKGROUND OF THE NEW PLANT

The present invention comprises a new and distinct cultivar of *Pelargonium×domesticum* known by the varietal name Maiden Lilac (Oglevee No. 717, Bodger No. 2 PD 18-5). The new variety was discovered in a selective breeding program by David Lemon at Bodger Seeds, Ltd., Lompoc, Calif. The new variety is a selection from the crossing of Morning Glory (Bodger No. 5 PD 63 unpatented) which is characterized by having a red purple flower with some white with Prince (U.S. Plant Pat. No. 8,090) wich has a medium purple flower with rich burgundy blotches, which parents are distinguishable from the claimed cultivar which has a vivid lavender bloom.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, and grown in a soilless media of constant fertilizer 150–200 parts per million of nitrogen and potassium has a response time of fourteen weeks from the rooted cutting to a flowering plant in a 6 inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristics was collected from asexual reproduction carried out by Oglevee Ltd. in Connellsville, Pa. The plant histories were taken on rooted cuttings believed to have been potted on approximately Feb. 1, 1996 and flowering on approximately Apr. 25, 1996 under full light and greenhouse, and colorings were taken indoors under 200–220 foot candles of fluorescent cool white light using The R.H.S. Colour Chart of The Royal Horticultural Society of London.

The Plant

Classification:
- *Botanical.*—*Pelargonium×domesticum.*
- *Commercial.*—Regal Geranium Maiden Lilac.

Form: Compact mound.
- *Height.*—16.0–18.0 cm above media.
- *Growth.*—Controlled.
- *Strength.*—Fast rooting, compact sturdy growth — no support needed.

Foliage: Stalked leaf attachment.

Leaves:
- *Size.*—6.0–7.5 cm.
- *Shape.*—Depressed ovate, cordate base.
- *Margin.*—Serrate margin.
- *Texture.*—Leathery, pubescent.
- *Color.*—Top: Yellow-green group 146 B. Bottom: Yellow-green group 148 B. Zone: None.
- *Ribs and veins.*—Palmate venation: Color: Yellow/green group 147C.

Petioles:
- *Length.*—5.0–6.5 cm.
- *Color.*—Yellow/green group 146C.

Stem:
- *Color.*—Yellow/green group 146D.
- *Internodes.*—1.5–2.0 cm.

The Bud (Umbell)

Shape: Elliptical Cluster.

Size: 2.0–2.5 cm.

Inflorescence

Blooming habit: Continuous.

Borne: Umbel; florets on pedicel; pedicel on peduncle.

Closed Florets:
- *Bud size.*—1.0–1.5 cm length, 0.5 cm width.

Size:
- *Fully open bloom.*—7.5–8.5 cm across.

Open florets:
- *Form.*—Cupped. Top: Purple Group 78A. Bottom: Violet Group 84C. Eye: Upper two petals Red-Purple group 59A. Lower three petals Red-Purple group 74B with white along edges to create a white "throat".
- *Petals.*—Five.
- *Size.*—4.5–5.5 cm.

*Texture and appearance.*—Satiny, appearance from a distance is a vivid lavender bloom above compact medium green foliage.

Petaloids

*Quantity.*—None.

Pedicel:

*Length.*—1.0–1.5 cm.

*Color.*—Yellow-green group 146C.

Peduncle:

*Length.*—5.5–6.0 cm.

*Color.*—Yellow-green group 146C.

Persistence:

*Disease resistance.*—Not known.

*Lasting quality.*—Unknown.

Reproductive Organs

Stamens:

*Anthers.*—3–4 mm in length.

*Filaments.*—Length: 1.4–2.0 cm. Color: White.

*Pollen.* Golden brown.

Pistils:

*Number.*—One.

*Length.*—1.5–1.8 cm.

*Stigma.*—Color: Red-purple group 60C; 5–6 parted.

*Style.*—Length 1.2–1.5 cm.

Ovaries:

*Color*—Pale Green. Pubescent; Superior.

*Length.*—5 mm.

Fruit: None.

General Characteristics

Maiden lilac is one of three colors in the new Maiden Regal Geranium series. The Regal "Maiden" series is a group of *Pelargonium×domesticum* varieties having large blooms with a compact medium plant size making them suitable for growing in a 5" pot. This series exhibits unique plant size, bloom size, and bloom color. Stock production is improved with many cuttings and quick rooting.

I claim:

1. A new and distinct variety of Geranium plant, substantially as shown and described.

* * * * *

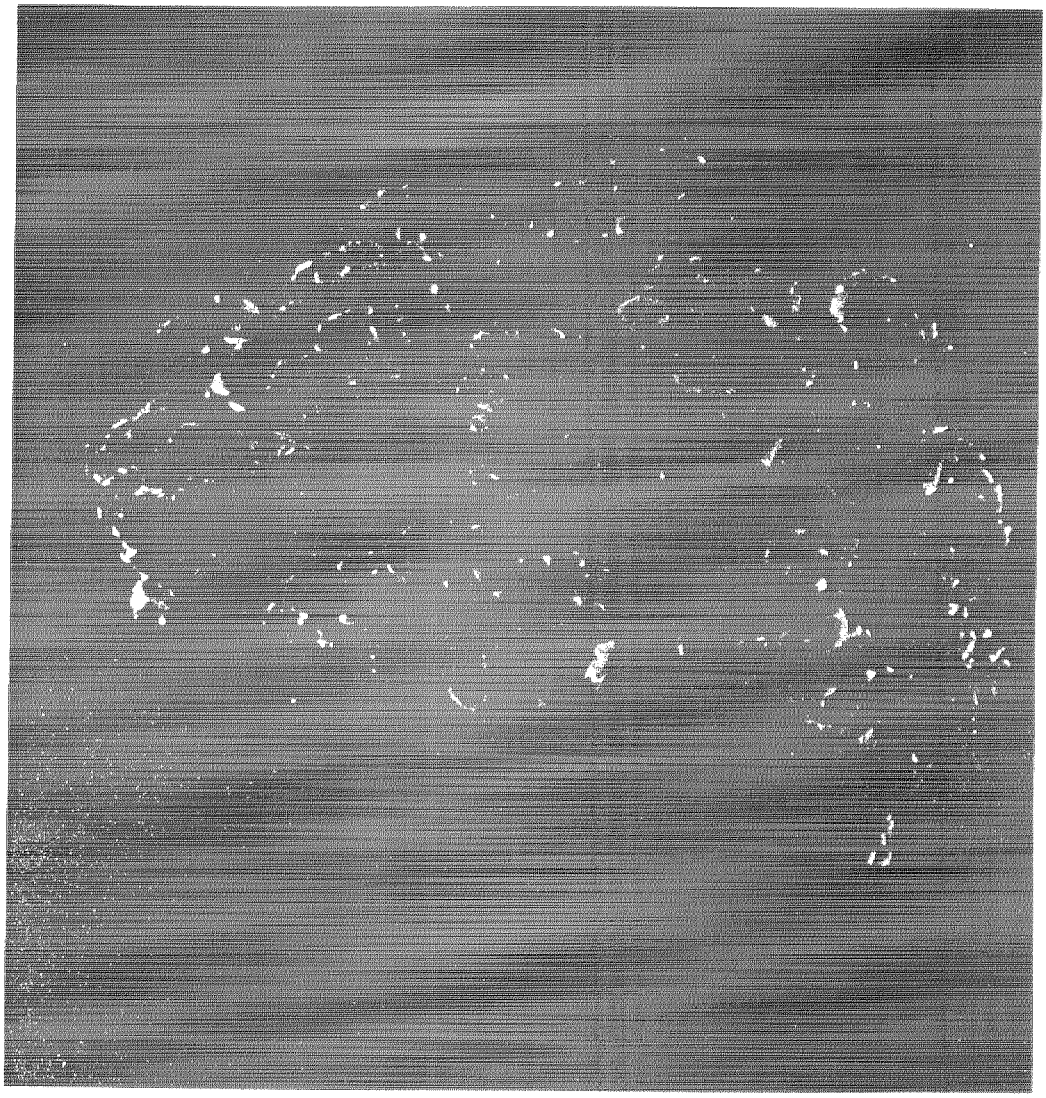

PLT-331 SR
C5203 OR PP 010,420